United States Patent
Larson et al.

(10) Patent No.: US 9,489,045 B2
(45) Date of Patent: Nov. 8, 2016

(54) METHODS AND APPARATUS FOR PROVIDING A SNAPSHOT TRUTHING SYSTEM FOR A TRACKER

(71) Applicant: HONEYWELL INTERNATIONAL INC., Morristown, NJ (US)

(72) Inventors: Brent D. Larson, Phoenix, AZ (US); Ken Leiphon, Phoenix, AZ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 14 days.

(21) Appl. No.: 14/669,336

(22) Filed: Mar. 26, 2015

(65) Prior Publication Data

US 2016/0282936 A1    Sep. 29, 2016

(51) Int. Cl.
| | |
|---|---|
| G01C 21/16 | (2006.01) |
| G08G 5/02 | (2006.01) |
| G01S 5/16 | (2006.01) |
| G06F 3/03 | (2006.01) |
| G06F 9/44 | (2006.01) |
| G09B 5/06 | (2006.01) |
| A61B 5/11 | (2006.01) |
| H04L 29/08 | (2006.01) |
| G05D 1/08 | (2006.01) |
| G01C 17/38 | (2006.01) |

(Continued)

(52) U.S. Cl.
CPC ........... *G06F 3/012* (2013.01); *G02B 27/0172* (2013.01); *G02B 27/0179* (2013.01); *G06F 3/017* (2013.01); *G02B 2027/014* (2013.01); *G02B 2027/0187* (2013.01)

(58) Field of Classification Search
CPC ..... G08G 5/025; G06F 3/346; A61B 5/1114; G01C 21/16
See application file for complete search history.

(56) References Cited

U.S. PATENT DOCUMENTS

| | | | | |
|---|---|---|---|---|
| 5,645,077 A | * | 7/1997 | Foxlin ................... | A61B 5/1114 600/587 |
| 5,978,715 A | * | 11/1999 | Briffe ................... | G05D 1/0808 244/1 R |

(Continued)

FOREIGN PATENT DOCUMENTS

| | | | | |
|---|---|---|---|---|
| EP | 2594197 | * | 5/2013 | ..... A61B 2560/0223 |
| JP | 2000065576 A | | 3/2000 | |

OTHER PUBLICATIONS

You, S., et al; Hybrid Inertial and Vision Tracking for Augmented Reality Registration; IEEE, 1999.

(Continued)

*Primary Examiner* — Lin Li
(74) *Attorney, Agent, or Firm* — Lorenz & Kopf, LLP

(57) ABSTRACT

A method for detecting and correcting drift associated with operation of a hybrid tracking system is provided. The method obtains a data signal from a first tracker subsystem having a first tracker latency time; for a defined window of time, the method captures snapshot input data for a second tracker subsystem having a second tracker latency time which is longer than the first tracker latency time; and captures synchronized data from the data signal which corresponds to the defined window of time; wherein the defined window of time comprises a time duration shorter than the second tracker latency time, to capture the snapshot input data. The method further determines a level of drift associated with operation of the first tracker subsystem; and adjusts operation of the first tracker subsystem according to the determined level of drift.

20 Claims, 5 Drawing Sheets

(51) Int. Cl.
*G01B 21/04* (2006.01)
*G02B 27/01* (2006.01)
*A61B 5/06* (2006.01)
*G06F 3/01* (2006.01)

(56) References Cited

U.S. PATENT DOCUMENTS

| | | | |
|---|---|---|---|
| 6,162,191 | A | 12/2000 | Foxlin |
| 6,474,159 | B1 * | 11/2002 | Foxlin ............... A61B 5/1114 73/488 |
| 7,640,106 | B1 * | 12/2009 | Stokar ................ G01C 21/16 342/147 |
| 8,761,434 | B2 | 6/2014 | Marks et al. |
| 8,953,154 | B2 * | 2/2015 | Galea .................... G01B 21/04 356/138 |
| 2002/0194914 | A1 | 12/2002 | Foxlin et al. |
| 2004/0080467 | A1 | 4/2004 | Chinthammit et al. |
| 2007/0122778 | A1 * | 5/2007 | Beitel ...................... G09B 5/06 434/219 |
| 2009/0043504 | A1 * | 2/2009 | Bandyopadhyay .... G01C 17/38 701/469 |
| 2011/0112996 | A1 * | 5/2011 | Tu ....................... G06F 3/0346 706/12 |
| 2012/0249807 | A1 | 10/2012 | Sugden |
| 2013/0041529 | A1 * | 2/2013 | He ........................ G08G 5/025 701/17 |
| 2013/0064427 | A1 * | 3/2013 | Picard .................... G01S 5/163 382/103 |
| 2014/0243671 | A1 | 8/2014 | Holl et al. |
| 2016/0035139 | A1 * | 2/2016 | Fuchs .................. G02B 27/017 345/633 |
| 2016/0112501 | A1 * | 4/2016 | Wheeler ............... H04L 67/104 709/204 |

OTHER PUBLICATIONS

Ribo, M. et al; Hybrid Tracking for Outdoor Augmented Reality Applications; IEEE, 2002.
World Viz; Hybrid Tracking; WorldViz 6 DOF Optical Inertial Hybrid Tracking Solution; PPT Studio 2013.
Jud, D. et al; Motion Tracking Systems; Studies on Mechatronics, An overview of motion tracking methods; Spring Term 2011.
Extended EP Search Report for Application No. 16161491.2-1557 dated Aug. 23, 2016.

* cited by examiner

METHODS AND APPARATUS FOR PROVIDING A SNAPSHOT TRUTHING SYSTEM FOR A TRACKER

TECHNICAL FIELD

Embodiments of the subject matter described herein relate generally to correcting drift errors associated with a tracker. More particularly, embodiments of the subject matter relate to drift correction associated with an inertial tracker system.

BACKGROUND

Tracker systems may be used to provide orientation and/or location data relating to a frame of reference, most typically as a function of time. Tracker systems can be self-contained within a moving subsystem (e.g., inertial trackers) or they can be spread across multiple frames of reference (e.g., optical, magnetic, acoustic, ultrasonic, mechanical, outside-in, inside-out). Exemplary tracker applications include navigation, remote monitoring, head-worn displays, guided munitions, simulators, device/computer input devices including the mouse, trackball, and gesture recognition. Multiple trackers may also be used together for redundancy, truthing, drift correction, or the like. In the case of inertial trackers, dual tracker systems may be compared to extract motion (translational and/or rotational) of a tracked object relative to a moving platform. In many cases, multiple relationships are stacked, one upon another, to yield a composite relation. One such example would be tracking an aircraft relative to the earth, calibrating or tracking a flight deck instrument relative to the aircraft, and tracking a head-worn display relative to the flight deck instrument.

Tracking the location and orientation of a head-worn display is a key aspect to providing meaningful information for certain display applications, such as displaying imagery that is conformal with the forward scene, and that is visible through optics that include a combiner element. Ideally, both a head-worn display and its associated tracker system would be small, lightweight, highly accurate, repeatable, very fast (i.e., high update rate with low latency) and low cost. Although an inertial tracker provides many of these characteristics and benefits, use of compact inertial trackers can also introduce tradeoffs in terms of accuracy, leading to inertial tracker output drift over time.

Accordingly, it is desirable to provide a system that also incorporates detection and correction of inertial tracker output drift. Furthermore, other desirable features and characteristics will become apparent from the subsequent detailed description and the appended claims, taken in conjunction with the accompanying drawings and the foregoing technical field and background.

BRIEF SUMMARY

Some embodiments of the present invention provide a method for detecting and correcting drift associated with operation of a hybrid tracking system. The method obtains a data signal from a first tracker subsystem having a first tracker latency time; and, for a defined window of time, captures snapshot input data for a second tracker subsystem having a second tracker latency time which is longer than the first tracker latency time; and captures synchronized data from the data signal which corresponds to the defined window of time; wherein the defined window of time comprises a time duration shorter than the second tracker latency time, to capture the snapshot input data. The method further calculates second tracker snapshot results from the captured snapshot input data for the second tracker subsystem; calculates first tracker snapshot results from the captured synchronized data from the first tracker subsystem; calculates an error between the first tracker snapshot results and the second tracker snapshot results, to determine a level of drift associated with operation of the first tracker subsystem; and adjusts operation of the first tracker subsystem according to the determined level of drift.

Some embodiments provide a head-worn display apparatus, configured to provide a conformal near-to-eye (NTE) display. The apparatus includes a hybrid tracking system, comprising: an inertial tracker, configured to provide first positional data of the head-worn display apparatus, with regard to an inertial reference frame; a non-inertial tracker, configured to provide second positional data of the head-worn display apparatus, with regard to the inertial reference frame; a snapshot module, configured to: determine a snapshot time frame by coordinating a window of time for gathering input data for the non-inertial tracker; synchronize operation of the inertial tracker and the non-inertial tracker; and capture a relevant subset of the first positional data associated with the determined snapshot time frame and a relevant subset of the second positional data associated with the determined snapshot time frame; a drift detection module, configured to compare the relevant subset of first positional data with the relevant subset of second positional data, to determine an offset; and a drift correction module, configured to adjust operation of the inertial tracker, based on the determined offset.

Some embodiments provide a non-transitory, computer-readable medium containing instructions thereon, which, when executed by a processor, perform a method. The method synchronizes an inertial tracker and a non-inertial tracker; identifies a snapshot time-frame, based on the synchronization step; during the snapshot time-frame, obtains input data for the non-inertial tracker; obtains data from the inertial tracker corresponding to the snapshot time-frame; obtains a first result from the inertial tracker and a second result from the non-inertial tracker, each representative of the snapshot time-frame; compares the first result to the second result to obtain a discrepancy result; and modifies operation of the inertial tracker, based on the discrepancy result.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION OF EMBODIMENTS

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter presented herein relates to methods and apparatus for detecting and correcting drift in tracker output data associated with a tracker system for a head-worn, near-to-eye (NTE) display using a "snapshot" data capture technique. During a short, defined time window, synchronized data are collected from more than one tracker. Generally, a low latency tracker provides rapid feedback during the operation of the NTE display, but can experience significant drift over time, skewing the feedback. The low latency tracker operates cooperatively with a high accuracy, but comparatively high latency, "truthing" tracker, which provides more precise data from which to correct the expected drift. The truthing tracker is further characterized, however, by having the ability to collect its raw input data within a short window of time, preferably comparable to or shorter than the latency or repetition period associated with the low latency tracker. By synchronizing and collecting data from both trackers in the same short window of time, a snapshot of comparative data is obtained. The snapshot data are then analyzed and compared to detect drift, and appropriate corrections may be made at the low latency tracker.

In the context of this application, "truthing" indicates corrections made to motion data generated by a high-speed, low latency tracker using more accurate motion data generated by a tracker that operates at a less-rapid pace. Also in the context of this application, the term "drift" includes the error, accumulated over time, which causes offset to an output data signal, such as that generated by a motion tracker. While described in the context of a near-to-eye display, the approach may be used for other systems, such as hand-held displays, remote motion systems or any device which benefits from the combination of light weight, fast response, high accuracy and low cost associated with the snapshot truthing approach.

Figure 1:
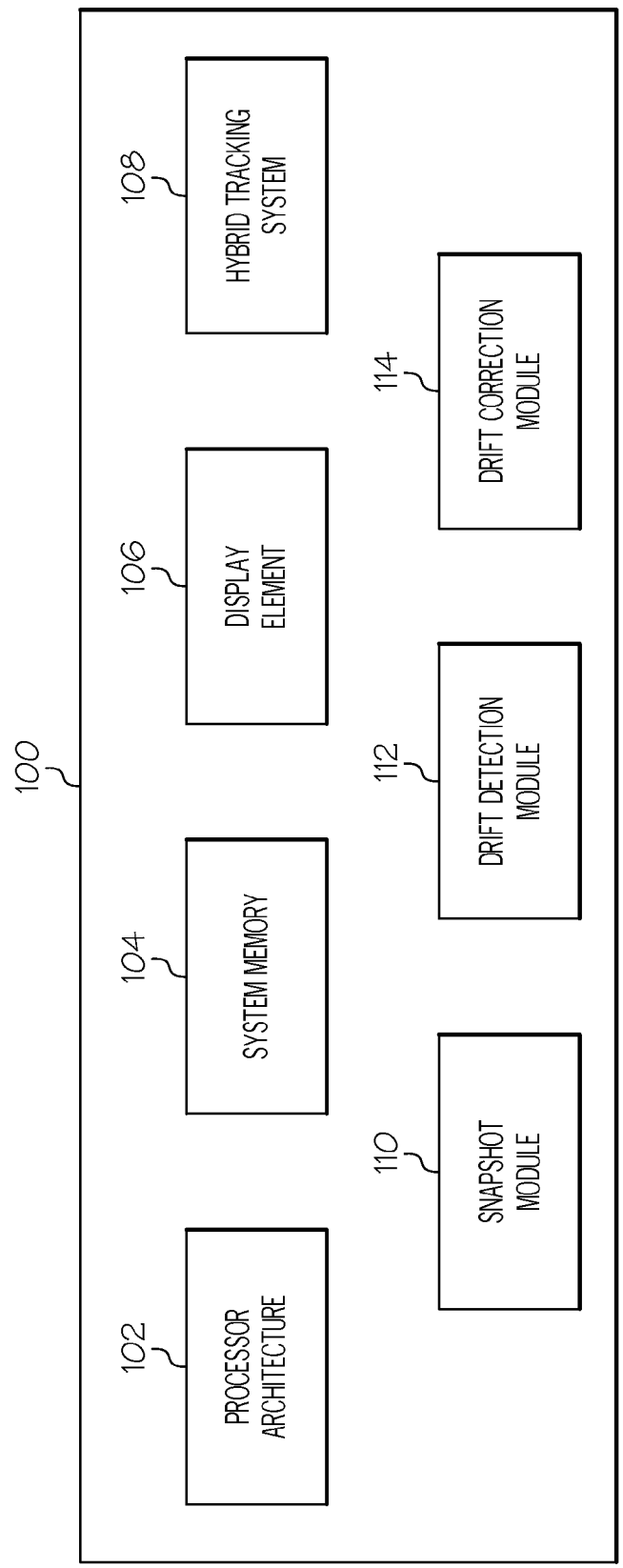
FIG. 1 is a functional block diagram of a snapshot truthing system, according to some embodiments.

Turning now to the figures, FIG. 1 is a functional block diagram of a snapshot truthing system 100, according to some embodiments. In practice, the system 100 that is schematically depicted in FIG. 1 would typically be realized as a system that spans two or more platforms exhibiting relative motion between the platforms. For example, a specialized avionics application might be configured to track a head-worn display relative to an aircraft flight deck. Such a system may also function in conjunction with other tracking systems which provide the relationship of the aircraft relative to the outside embodiment. Other snapshot truthing implementations are of course possible which involve a single platform, for example combining a low latency inertial system with a drift-immune but slower inertial system. A snapshot truthing system 100 may be implemented as one or more of: a programmable hardware element incorporated into a near-to-eye (NTE) display, processing logic incorporated into a computer system, a general purpose machine, a specialized avionics system, or the like.

As depicted, the snapshot truthing system 100 includes, without limitation: a processor architecture 102; a system memory 104; a head-worn display 106; a hybrid tracking system 108; a snapshot module 110; a drift detection module 112; and a drift correction module 114. These elements and features of the snapshot truthing system 100 may be operatively associated with one another, coupled to one another, or otherwise configured to cooperate with one another as needed to support the desired functionality—in particular, detecting and correcting drift in the output of a tracking system using snapshot truthing techniques, as described herein. For ease of illustration and clarity, the various physical, electrical, and logical couplings and interconnections for these elements and features are not depicted in FIG. 1. Moreover, it should be appreciated that embodiments of the snapshot truthing system 100 will include other elements, modules, and features that cooperate to support the desired functionality. For simplicity, FIG. 1 only depicts certain elements that relate to the snapshot truthing techniques described in more detail below. In an exemplary embodiment, each of the various components and subsystems would be located with one of the platforms or frames of reference associated with the tracked degrees of freedom, but this is by no means required. As an example for an avionic NTE tracker system, the hardware and processing capability could include eyewear-mounted portions, body-worn components, aircraft-mounted systems as well as other involved subsystems such as databases that are external to the aircraft.

The processor architecture 102 may be implemented or performed with one or more general purpose processors, a content addressable memory, a digital signal processor, an application specific integrated circuit, a field programmable gate array, any suitable programmable logic device, discrete gate or transistor logic, discrete hardware components, or any combination designed to perform the functions described here. In particular, the processor architecture 102 may be realized as one or more microprocessors, controllers, microcontrollers, or state machines. Moreover, the processor architecture 102 may be implemented as a combination of computing devices, e.g., a combination of digital signal processors and microprocessors, a plurality of microprocessors, one or more microprocessors in conjunction with a digital signal processor core, or any other such configuration.

The system memory 104 may be realized using any number of devices, components, or modules, as appropriate to the embodiment. Moreover, the snapshot truthing system 100 could include system memory 104 integrated therein and/or system memory 104 operatively coupled thereto, as appropriate to the particular embodiment. In practice, the system memory 104 could be realized as RAM memory, flash memory, EPROM memory, EEPROM memory, registers, a hard disk, a removable disk, or any other form of storage medium known in the art. In certain embodiments, the system memory 104 includes a hard disk, which may also be used to support functions of the snapshot truthing system 100. The system memory 104 can be coupled to the processor architecture 102 such that the processor architecture 102 can read information from, and write information to, the system memory 104. In the alternative, the system memory 104 may be integral to the processor architecture 102. As an example, the processor architecture 102 and the system memory 104 may reside in a suitably designed application-specific integrated circuit (ASIC).

The display element 106 is configured to provide a visual representation of imagery, some or all of which may be conformal with a scene or portion of the user's environment that is visible through optics that include a combiner element. The display element 106 is generally implemented with a head-worn, near-to-eye (NTE) display, including associated collimating optics. Other embodiments of a display element 106 may include handheld or body-worn devices, or displays mounted to helmets, body suits, equipment or similar devices with the ability to move with respect to their environment. Motion data, commonly involving location and/or orientation, associated with operation of the display element 106 is used to generate the visual presentation to a user, and to calculate and generate future visual presentations.

Figure 2:
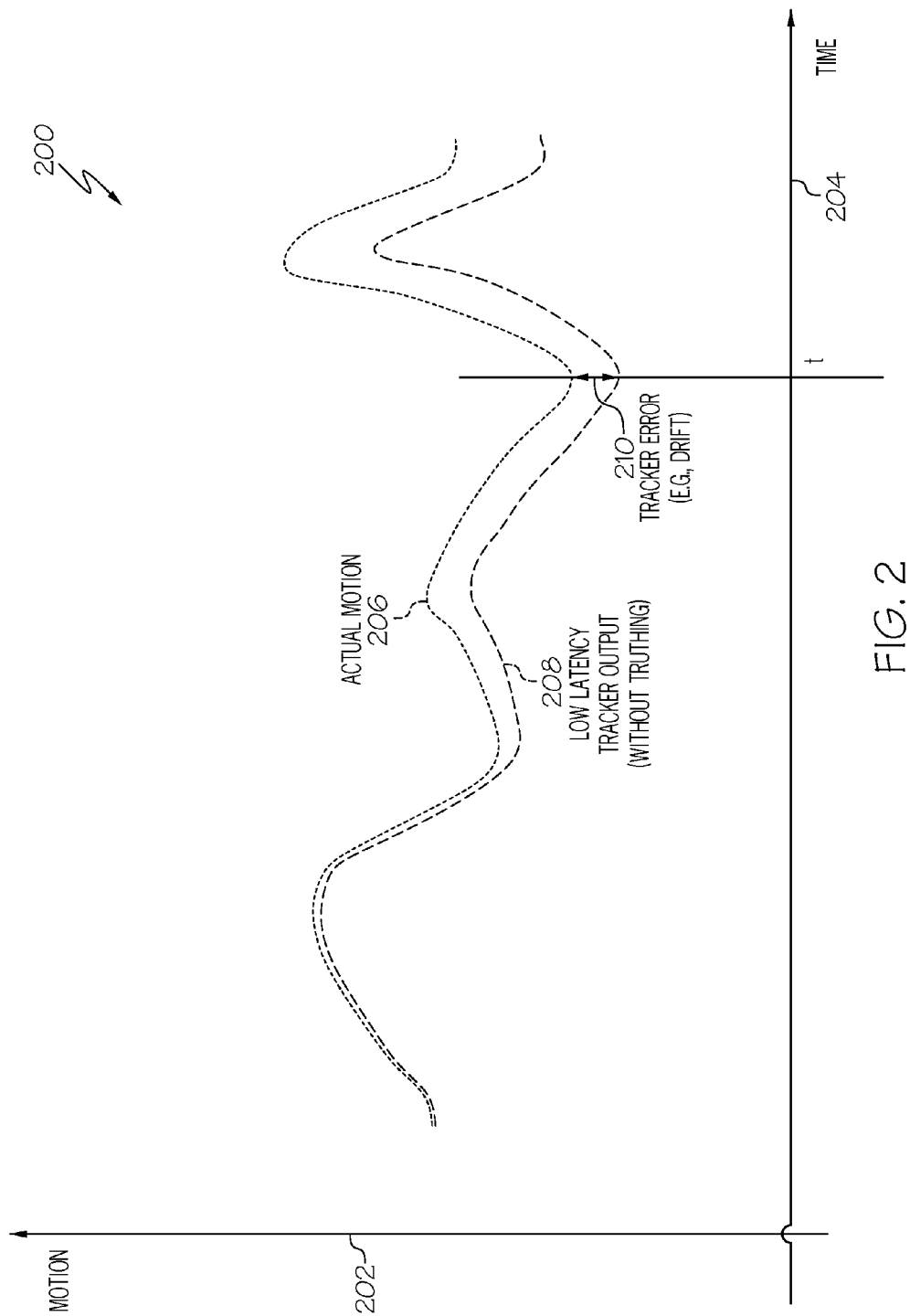
FIG. 2 is a graph depicting an actual motion signal and a motion signal generated by a low latency tracker, versus time.

The hybrid tracking system 108 is configured (in the embodiment of FIG. 1) to detect and provide orientation and/or location data for the display element 106. Data associated with these parameters is obtained using a combination of tracker subsystems. The first of the tracker subsystems is preferably implemented using a high speed, low latency tracker, such as an inertial tracker. Inertial trackers are self-contained within a moving subsystem, and use accelerometers, gyros, or the like, to provide positional parameter data such as location and/or orientation. (Generally, the term "position" may refer to one or more of: orientation data, location data, and/or other degrees of freedom.) Additionally, inertial trackers may provide data on how these positional parameters change over time. In the case of relative motion between two platforms, the positional parameters could represent differential location and/or orientation between two inertial tracker subsystems, the two subsystems preferably having similar or identical characteristics. During operation of a low latency tracker, inaccuracies can be common and present themselves in the form of "drift" (i.e., error in the output signal). In the exemplary embodiment of typical compact and lightweight inertial trackers, this error increases over time, as the erroneous output signal data are used for future calculations and output generation in an integrative or summing fashion. The concept of drift is illustrated in FIG. 2, which is a graph 200 depicting an actual motion signal and a motion signal generated by a low latency tracker, versus time 204. The graph 200 illustrates accumulated errors, for example, in a drift-prone inertial tracking system. The horizontal axis represents time 204 and the vertical axis represents a positional parameter (e.g., a degree of freedom) 202 of the associated motion. As shown, an actual motion signal 206 represents a theoretically ideal, error-free version of an output tracker signal, based on a sample of motion. However, the low latency tracker output signal 208 illustrates a real-world example of an output tracker signal, based on the same sample of motion, that includes signal "drift" due to inherent imperfections, defects, and/or errors occurring during operation of the hardware of the low latency tracker. Here, the difference between the actual motion signal 206 and the low latency tracker output signal 208 is represented by the calculated tracker error 210. The tracker error 210 is the accumulated amount of drift that has occurred, over time, when the actual motion signal 206 and the low latency tracker output signal 208 are compared at a point in time, t.

It should be noted that FIG. 2 depicts the calculated tracker error 210 as a single scalar value for simplicity, however, the errors measured will typically include errors associated with multiple degrees of freedom (e.g., 3-DOF, 6-DOF, or more). As an example of more than 6-DOF, the tracker subsystem could additionally monitor a varying relationship between two partially coupled objects, such as the separation between two near-to-eye (NTE) oculars included in a head-worn display. This separation might be an adjustable parameter related to the inter-pupillary distance (IPD) of the wearer of the display, and could include other location and angular offsets between the two oculars as well. In one embodiment, each of the two oculars could include a low latency tracker. In another embodiment the two ocular assembly would share a low latency tracker, with the differential position between the two oculars being monitored and measured at the reduced rate associated with the truthing tracker subsystem.

Returning to FIG. 1, the exemplary inertial tracking subsystem is therefore combined with a repeatable, high-accuracy tracking subsystem which is not subject to cumulative drift over time in the same manner or to the same extent, to form the hybrid tracking system 108. This second tracking subsystem may be referred to as a "truthing" subsystem, which is used to maintain and/or restore the fidelity of the drift-prone low latency subsystem (e.g., the inertial or differential-inertial tracker subsystem). The truthing subsystem may be implemented using a non-inertial tracker, including, without limitation: an optical tracker, a magnetic tracker, an acoustic tracker, an ultrasonic tracker, a mechanical tracker, or the like.

The truthing subsystem generates a tracker output signal that reflects the position of the display element 106 more accurately than the inertial tracking subsystem, preferably with comparable precision. However, because the truthing subsystem is subject to additional latency, the signal output has a lower update rate and lags considerably behind the signal output generated by the high-speed inertial tracker. The signal output from the truthing subsystem is therefore used to make subsequent, and possibly retroactive corrections to the signal output from the inertial tracker subsystem, and to decrease the drift, or accumulated error in the inertial tracker subsystem output signal over time.

The snapshot module 110 is suitably configured to determine an applicable "snapshot" window of time, and to capture a "snapshot" of data generated by the hybrid tracking system 108 during this snapshot window of time for further analysis. As used herein, the term "snapshot" refers to capturing a synchronized data set. Further, a "snapshot" window of time refers to a very short time frame during which snapshot data, and in particular the raw input truthing data, are acquired. To determine an appropriate snapshot window (e.g., applicable short time-frame), the snapshot module 110 synchronizes operation of the inertial tracker subsystem and the non-inertial tracker subsystem (of the previously-described hybrid tracking system 108). More specifically, the snapshot module 110 synchronizes a signal associated with the inertial tracker subsystem to an input signal of the non-inertial tracker subsystem. The snapshot module 110 is further configured to capture the relevant subset of motion data (e.g., input data for the truthing tracker, input and/or output data for the low latency tracker, and possibly additional data to support calculating an estimate of translational velocity, rotational velocity or both) generated by the hybrid tracking system 108, during the determined snapshot window of time. While the term "snapshot" is particularly familiar for an optical system involving image capture, it is not intended to be limiting in that respect. In the context of this application, the snapshot window of time corresponds to the data collection window for raw input data to the truthing tracker for a given measurement cycle. In the example of a camera-based system, this corresponds to the exposure or integration time of the camera, or in the case of multiple cameras, corresponds to a temporal window which brackets the exposure time for the set of cameras.

In the context of this application, we will consider the snapshot window of time as corresponding to the data collection window for raw input data to the truthing tracker for a given measurement cycle. In the example of a camera-based system, this would correspond to the exposure or integration time of the camera or, in the case of multiple cameras, would correspond to a temporal window which brackets the exposure times for the set of cameras.

The synchronization between the low latency (e.g., inertial) tracker and the truthing tracker can follow any of several embodiments or variations thereof. The underlying snapshot time window is the collection window for the raw input data for the truthing tracker subsystem. Once this raw input data is eventually converted to a meaningful output format (e.g., via image analysis in the case of a camera-based truthing approach), it will be compared with one or more low latency samples closely correlated in time with the collection of that input data. The corresponding data collected for or from the low latency tracker could be either input data, output data, or both, and in the case of an inertial tracker would typically include one or more preceding iterations of data as well. Such synchronization options will be described in more detail below. In the context of this application, the result to be compared with the truthing tracker result will be referred to as the synchronized corresponding result, or corresponding result for short. Again, said corresponding result represents and is derived, at least in part, from the afore-mentioned corresponding data.

The drift detection module 112 is configured to determine a level of accumulated drift associated with motion of the display element 106, using the snapshot data obtained by the snapshot module 110. The drift detection module 112 performs a comparison between output data (corresponding result) generated by the inertial tracker subsystem (of the hybrid tracking system 108) and output data generated by the truthing (e.g., non-inertial) tracker subsystem, based on the synchronized data snapshot described above. The drift detection module 112 uses the results of this comparison to determine an amount of accumulated error (i.e., drift) as of the time window associated with the snapshot. In certain embodiments, the amount of accumulated error includes a two-dimensional offset in position. One such example would be an implementation of a pointing device, computer mouse or similar device to indicate a location on a two-dimensional image screen. However, in many embodiments, such as the head-worn display system, the amount of accumulated error is associated with higher numbers of degrees of freedom (DOF) and involves three-dimensional location, orientation, and possibly other positional relationships.

The drift correction module 114 is configured to adjust operation of the hybrid tracking system 108, based on the amount of drift determined by the drift detection module 112. More specifically, for the inertial tracking embodiment, the drift correction module 114 makes adjustments or modifications to the operation of the inertial tracker subsystem, to counteract the detected amount of drift and to increase and maintain the accuracy of the generated output of the inertial tracker subsystem. Increased accuracy of the generated output enables increased accuracy of the content presented via the display element 106, with regard to orientation, location, and/or rates of change thereof. In the previously described embodiment of a binocular head-worn display with adjustable but tracked inter-ocular positional relationship, this can also serve to reduce or eliminate vergence errors such as vertical disparity, cyclodisparity or incorrect binocular distance.

In practice, the snapshot module 110, the drift detection module 112, and/or the drift correction module 114, may be implemented with (or cooperate with) the processor architecture 102 to perform at least some of the functions and operations described in more detail herein. In this regard, aspects of the snapshot module 110, the drift detection module 112, and/or the drift correction module 114, may be realized as suitably written processing logic, application program code, or the like.

Figure 3:
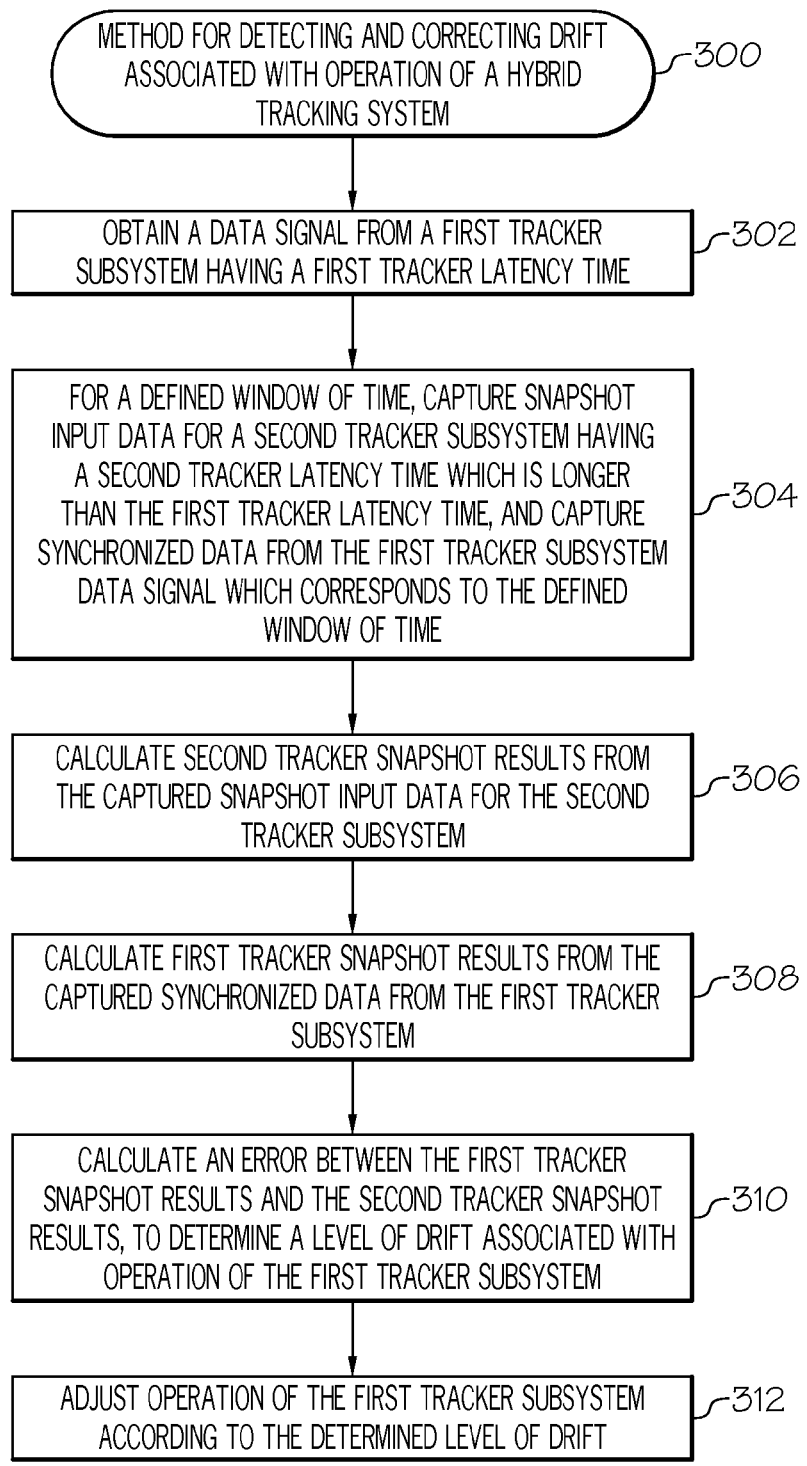
FIG. 3 is a flowchart that illustrates an embodiment of a process for detecting and correcting drift associated with operation of a hybrid tracking system.

FIG. 3 is a flowchart that illustrates an embodiment of a process 300 for detecting and correcting drift associated with operation of a hybrid tracking system. The various tasks performed in connection with process 300 may be performed by software, hardware, firmware, or any combination thereof. For illustrative purposes, the following description of process 300 may refer to elements mentioned above in connection with FIGS. 1-2. In practice, portions of process 300 may be performed by different elements of the described system, e.g., a display element, a hybrid tracking system, a snapshot module, a drift detection module, and/or a drift correction module. It should be appreciated that process 300 may include any number of additional or alternative tasks, the tasks shown in FIG. 3 need not be performed in the illustrated order, and process 300 may be incorporated into a more comprehensive procedure or process having additional functionality not described in detail herein. Moreover, one or more of the tasks shown in FIG. 3 could be omitted from an embodiment of the process 300 as long as the intended overall functionality remains intact.

For ease of description and clarity, it is assumed that the process 300 begins by obtaining data, for example representative of either input or output signals, from a first tracker subsystem having a first tracker latency time (step 302). The first tracker subsystem is generally implemented using a high speed, low latency tracker, such as an inertial tracker. The first tracker subsystem utilizes input data and typically recent prior data to generate an output signal including motion data (e.g., orientation and/or location data) collected over time, wherein the motion data are associated with the operation of a head-worn display.

Next, for a defined window of time, also referred to herein as the snapshot window of time, the process 300 synchronizes the data signal from the first tracker subsystem with an input signal to a second tracker subsystem (not shown). As described previously, the input signal to the second tracker subsystem is provided in the form of raw data collected by the second tracker system during that snapshot window of time, and the synchronization method can take any of several forms. The defined window of time can be synchronized with respect to the time when the first tracker output is finalized and available. Alternately, the defined window of time can be synchronized to the collection time of the most recent input data used to calculate that first tracker output. A third option is to synchronize the defined window of time to an interpolation of the first tracker outputs, by comparing the defined window of time to the output times of adjacent tracker outputs. Yet another option is to synchronize the defined window of time to an interpolation of adjacent tracker outputs based upon their corresponding input data times. Interpolation would typically be used, for example, if the two tracker timings are not locked in phase, and said interpolation could take many forms, such as linear interpolation, non-linear interpolation, or other similar numerical estimation methods (e.g., curve fitting) involving two or more sequential outputs from the first tracker system.

Then, for the defined window of time, the process 300 captures snapshot input data for a second tracker subsystem having a second tracker latency time which is longer than the first tracker latency time, and captures synchronized data from the first tracker subsystem data signal which corresponds to the defined window of time (step 304). In other words, the process 300 captures first snapshot data from the first tracker subsystem and second snapshot data from the second tracker subsystem, based on the synchronized corresponding data signal for the first tracker subsystem and the synchronized input signal for the second tracker subsystem. In certain embodiments, the first snapshot data comprises an inertial estimate of position (e.g., orientation and/or location), relative to a reference frame, from the first tracker subsystem, and the second snapshot data comprises raw data that will subsequently lead to a non-inertial estimate of position from the second tracker subsystem. Here, the process 300 collects motion data input or output signals from the first tracker subsystem (e.g., the inertial tracker) and input data to the second tracker subsystem (e.g., the non-inertial tracker). The process 300 limits this data collection to the motion data signals produced during (or otherwise representative of) the defined snapshot window of time. In other words, the collected motion data are delineated by the beginning point and endpoint of the defined window of time. In certain embodiments, the defined window of time is determined by the process 300 prior to synchronization of the applicable signals. In other embodiments, however, the defined window of time is predetermined information that is communicated to the process 300 for use in signal synchronization and data capture. The exact timing and duration of the snapshot window of time can depend upon many considerations and parameters, such as whether the tracker subsystems are phase-locked or not, but the key requirement is that the snapshot captures data for each tracker subsystem that can be meaningfully compared, despite any disparity, however large, in tracker latencies.

As defined herein, the snapshot or defined window of time comprises a raw input data collection window associated with the second tracker subsystem, during which the Second Snapshot Data are collected. In some embodiments, the first data collection window and the second data collection window are synchronized by being temporally coordinated or synchronous. In other embodiments, however, the first data collection window and the second data collection window are asynchronous (e.g., not phase-locked), but the more frequent updates from the low latency system may be interpolated to best correspond with the data collection window of the truthing system, allowing for a First Snapshot Data result that is effectively synchronized with the Second Snapshot Data. Alternatively, the snapshot data collection window for the truthing system may be temporally contained within the most recent collection window or interval for the low latency (e.g. inertial) system. Here again, it is noted that such an inertial system relies upon a potentially large set of prior data in addition to the most recent data.

Once the process 300 has captured first and second snapshot data, the process 300 calculates second tracker snapshot results from the captured snapshot input data for the second tracker subsystem (step 306), and calculates first tracker snapshot results from the captured synchronized data from the first tracker subsystem (step 308).

The process 300 then calculates an error between the first tracker snapshot results and the second tracker snapshot results, to determine a level of drift associated with operation of the first tracker subsystem (step 310). This calculation (step 310 of process 300) is not constrained in any meaningful way by the low latency of the first tracker subsystem. Rather, the duration or elapsed time for this step is most closely associated with the latency of the second tracker subsystem, which is typically longer than the first tracker latency, possibly even one or more orders of magnitude longer. This latency could include allowances for substantial amounts of computational time, verification of results based on multiple measurements, low cost implementations, etc. The process 300 then adjusts operation of the first tracker subsystem according to the determined level of drift (step 312). In certain embodiments, the calculated error includes a translational offset, which may be added to current location data to correct the generated output of the first tracker subsystem (e.g., the inertial tracker). In some embodiments, however, the calculated error is associated with other, possibly multiple, orientational degrees of freedom (DOF), and the process 300 performs a rotational computation to correct the generated output of the first tracker subsystem. In the more general case, both of these errors may apply, along with potential errors in other tracked degrees of freedom, if any.

In some embodiments, the process 300 calculates an average or weighted average of the recently calculated error and a plurality of previously calculated errors, and determines the level of drift based on the calculated average or weighted average. The correction applied to the generated output signal of the first tracker subsystem in this case uses an average or a weighted average of a set of recent calculated errors. Here, it is desirable to exclude truthing measurements that are readily recognized to be spurious, such as in the case of recognizable obscuration or other interference with the truthing tracker. For example, truthing measurements recognized to be spurious may be ascribed a zero weighting factor.

In other embodiments, data indicative of the rate of change of position (location or orientation) are collected along with the other snapshot data. One such embodiment involves collection of one or more preceding low latency data sets, allowing the calculation of a translational and/or rotational velocity estimate at the time of the snapshot. Given that additional information for the snapshot, the relative weight of that snapshot can be adjusted relative to the weight of other snapshot results when calculating a weighted average. In cases where detected velocities are significantly higher than prior or subsequent snapshot results, the results from a given snapshot can be ascribed a reduced or even zero weighting or be otherwise ignored. The snapshot approach enables this by appropriately recognizing and leveraging the relatively slower drift characteristics when compared with the low latency timing of the first tracker.

In some embodiments, the correction can be applied abruptly as soon as an error is determined, which is appropriate if the errors are small and not likely to be distracting or bothersome during operation of the head-worn display or other involved system. Alternatively, the correction can be applied gradually. In one embodiment, correction rates for each degree of freedom can be limited to a corresponding maximum rate per unit time, such that large corrections may take multiple, or perhaps many cycles to accomplish. In other embodiments, the rate of correction application may be determined by applying a scale factor to the total error. In still other embodiments, additional rules or algorithms for distributing the correction over time may be utilized.

In certain embodiments, a correction is applied each time an error is calculated between the two signals. In other embodiments, however, the process 300 considers multiple successive calculated errors prior to applying corrections. For example, the process 300 may recognize spurious or anomalous measurements by comparing the successive calculated errors and watching for changes that are consistent with drift. For example, if the user raises a hand or arm and obscures one or more optical sensors, the analysis system can recognize this as one or more outliers or erroneous truthing samples. In one embodiment, correction is not applied until a predetermined number of valid samples indicate a reasonably consistent error value, for example a constant calculated error value or a gradually changing calculated error value. The process 300 may determine whether the calculated error is consistent with a previously calculated error (or a plurality of previously calculated errors), and when these values are consistent, adjusting operation of the first tracker subsystem. Again, relative weighting of recent error values may be considered, for example based upon sensed rates of motion.

In another embodiment, correction is additionally applied when the calculated errors are quite large but the truthing tracker output is relatively smooth over a small but non-zero range. This would be consistent with a realignment of the two trackers following an event such as power-up, extended obscuration, storage or similar.

Adjustment and/or modification of the operation of the first tracker subsystem includes altering the generated output signal to correct the produced motion data according to the detected level of drift. Motion data associated with operation of the head-worn display is used to generate the visual presentation to a user, and to calculate and generate future visual presentations. Correcting the motion data produced by the first tracker subsystem not only restores accuracy to the present visual display, but also ensures increased accuracy in the calculations for future visual displays. The process 300 adjusts operation of the first tracker subsystem to remove an accumulated level of drift, after analysis of a set of snapshot data, and to prevent the current level of drift from increasing the generated error over time, which would affect the orientation of the visual presentation in the future.

Figure 4:
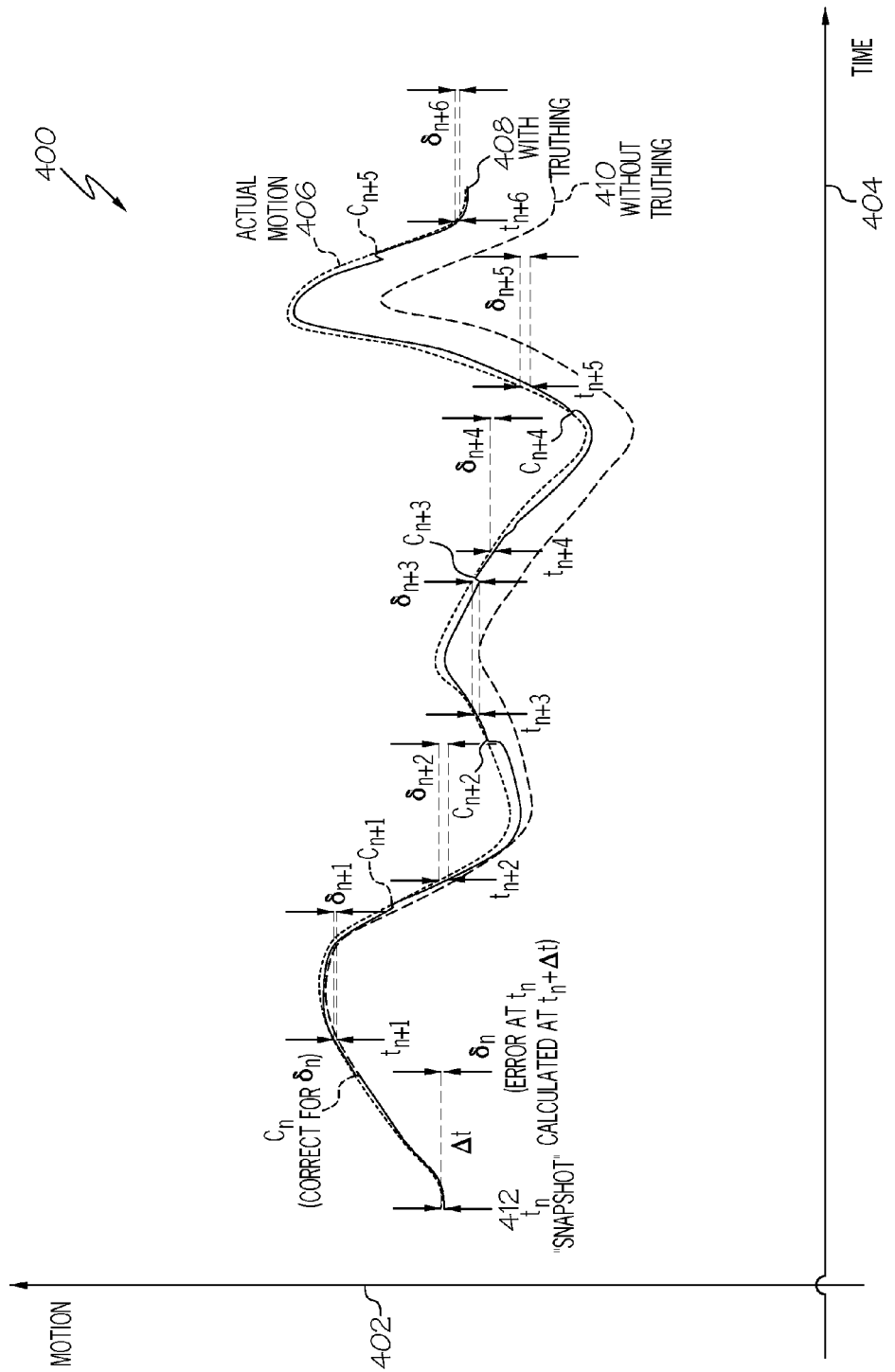
FIG. 4 is a graph depicting an actual motion signal, a motion signal generated by a low latency tracker, and a corrected motion signal generated by a low latency tracker.

Further detail related to an embodiment of process 300 is illustrated in FIG. 4. FIG. 4 is a graph 400 depicting an actual motion signal 406, a motion signal generated by a low latency tracker (e.g., a motion signal without "truthing" 410), and a corrected motion signal generated by a low latency tracker (e.g., a motion signal with "truthing" 408). In the context of this application, "truthing" indicates corrections made to motion data generated by a high-speed, low latency tracker using more accurate motion data generated by a tracker that operates at a less-rapid pace. The graph 400 illustrates how a snapshot-truthing approach enables high precision output with a long latency truthing system.

As shown, the horizontal axis represents time 404 and the vertical axis represents motion 402, e.g., showing changes associated with one or more degrees of freedom as a function of time. As described previously with regard to FIG. 2, an actual motion signal 406 represents a theoretically ideal, error-free version of an output tracker signal, based on a sample of motion. However, the output signal that is generated in reality is represented by the motion signal without truthing 410. The motion signal without truthing 410 includes a level of drift which accumulates over time 404, and is significantly different than the actual motion signal 406. In this particular example, over time, accumulated error (e.g., drift) causes the motion signal without truthing 410 to skew toward a lower value for the plotted degree of freedom (e.g., location along an axis, or rotation about an axis) than that of the actual motion signal 406.

Also shown is the motion signal with truthing 408, illustrating the generated motion signal when truthing techniques are used to correct for the accumulated drift over time, as described above with regard to process 300 in FIG. 3. Here, a snapshot 412 of motion data is taken at time $t_n$, wherein motion data are collected for a very short window of time. Some examples for defining this short window of time have been described in earlier paragraphs. The snapshot 412 includes raw input data collected by a non-inertial tracker (and subsequently processed to yield synchronized results to compare with corresponding inertial results) and corresponding snapshot data associated with an inertial tracker (e.g., a low latency tracker). The sets of motion data are processed and then compared to calculate an error between the two output signals, which is shown as $\delta_n$. Obtaining the snapshot 412 data is shown to occur at time $t_n$. The actual snapshot window cannot, of course, be truly instantaneous, but the window duration is preferably negligible on the time scale in FIG. 4. Hence it is a best estimate of the position during that short window of time of the associated motion. Processing of the snapshot data, especially the data collected by the non-inertial tracker is shown to take an amount of time, $\Delta t$, and calculation of the error occurs at time $t_n + \Delta t$. As shown, corrections ($C_n$) to the motion signal with truthing 408 are made at time $t_n + \Delta t$, indicating that corrections in this particular example occur as soon as the error $\delta_n$ is calculated. Additional snapshots ($t_n$ through $t_{n+6}$) of generated motion data are taken throughout the graph 400. For each snapshot, an error ($\delta_n$ through $\delta_{n+6}$) is calculated, and then a correction ($C_n$ through $C_{n+6}$) is made to the motion signal with truthing 408, based on the calculated error. Due to the corrections ($C_n$ through $C_{n+6}$) made throughout the graph 400, the motion signal with truthing 408 is very similar to the actual motion signal 406, and represents significantly less accumulated error than the motion signal without truthing 410.

The interval $\Delta t$ can be any value, but is preferably longer than the latency time of the low latency tracker, because allowing extra time can bring significant benefits relating to system tradeoffs. As shown, $\Delta t$ is somewhat smaller than the time between truthing samples, but can also be longer than that time. The interval between truthing samples is shown as consistently equal, but that is not required. The primary requirement is that the "snapshot" data collection window for the truthing tracker is short, and the corresponding or correlated result for the low-latency tracker is also representative of its output from during the same synchronized time frame. The truthing samples could be collected as frequently or infrequently as desired. That frequency could be based upon the truthing method used, computational power or complexity, cost considerations, and so forth, but preferably before error magnitudes associated with drift exceed desired tracking tolerances. The correction ($C_n$) is shown as being applied quickly but not instantaneously. The manner in which the correction is applied can vary based on the system design as well as varying based upon the collected data.

Figure 5:
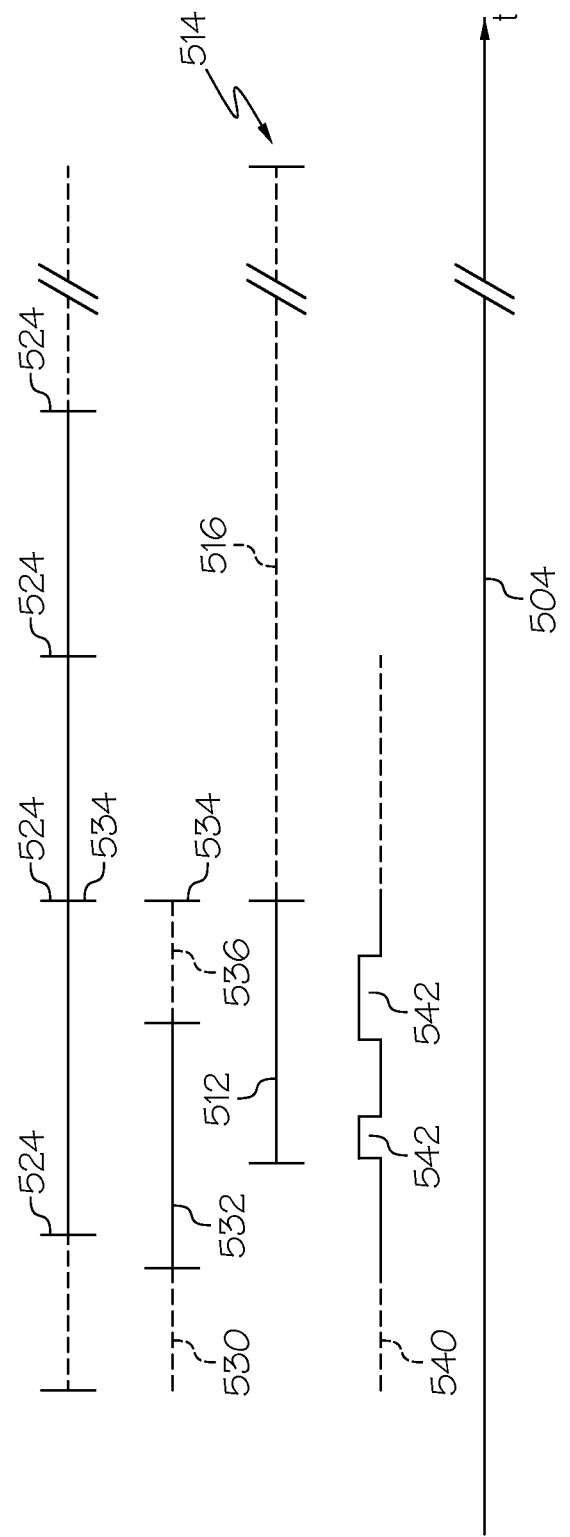
FIG. 5 is a timing chart showing tracker synchronization, according to one embodiment.

An exemplary timing relationship between the corresponding snapshots for the low latency tracker subsystem and the truthing tracker subsystem is shown in FIG. 5. Axis 504 represents elapsed time t. Input data to the truthing tracker system is collected during snapshot time window 512, processed during the interval 516, and eventually results in a truthing output data set at time 514. The break marks in axis 504 and matching marks in other sequences represent the possibility of extended latency times before result 514 becomes available. The sequential outputs of the low latency tracker are represented by points in time 524, and are typically, though not necessarily, periodic along the time axis (t). Time 534 represents one such low latency tracker output time, and is calculated or otherwise extracted, during time window 536, from input data collected during input time window 532 and possibly prior results represented by 530. The truthing snapshot corresponds to snapshot window 512, whereas the corresponding low latency snapshot can be associated with window 532, result 534, window 536 or combinations thereof. If the relative phase of the two trackers is consistent over time, then the snapshot window and corresponding low latency snapshot to be compared preferably maintain a constant relationship to each other. If the phase is not consistent, then the output (available at time 514) from snapshot time window 512 would preferably be compared to a weighted average resulting from two or more sequential low latency snapshots in the temporal vicinity of snapshot window 512.

In one embodiment, a camera-based system is used as the truthing tracker for a differential inertial tracker system to monitor the spatial relationship between two reference frames. A first reference frame and a second reference frame (e.g., a headset and a flight deck) are each fitted with low latency inertial tracker subsystems, with the relative difference in outputs being used as the composite low latency output. The truthing tracker combines at least one camera with a fixed relationship to one of the two reference frames, and a set of optical targets (e.g., IR LEDs, passive targets or features, or similar) affixed to the other reference frame. In this embodiment, the time window 512 of FIG. 5 corresponds to the active shutter time of the camera. The time window 512 is preferably very short to minimize any blur or similar motion-related artifacts in the captured and subsequently analyzed image data or snapshot. However, in other embodiments, even such motion-related artifacts may be utilized to advantage. The degree of blur can be analyzed to extract further information about motion during the snapshot duration. Various algorithms can be utilized, such as finding the range of motion during the snapshot, locating the centroid of the blurred image, or possibly other aspects. These pieces of extracted information can be combined with the low latency snapshot data to better estimate the appropriate correction offset(s) or to determine the presence of spurious or anomalous data for which alternate weighting should be considered, as discussed earlier.

Yet another variant, in the case of actively emitting camera targets, would be to pulse the emitter(s) one or more times during the short collection window. This is depicted as pulses 542 in FIG. 5. If a single pulse were utilized during the snapshot collection window 512, this would have the effect of reducing the effective snapshot duration for the associated tracker data even further. This will likely reduce the blur. Providing for multiple pulses within the window can even provide multiple closely spaced image spots in the case of rapid motion, again providing additional velocity information for determination of offsets or weighting factors. Further, by utilizing an asymmetric set of pulses 542 (e.g., varying amplitudes, varying pulsewidths as shown in FIG. 5, or varying pulse spacings), any discernable separation(s) could facilitate identification of the direction of the detected velocity, which could be used to further corroborate the performance of the low-latency tracker system. Emitter output 540 outside of the collection window 512 would preferably be zero, but this would not be necessarily required in the case of an effective shuttering mechanism or related method for limiting the snapshot collection window.

Techniques and technologies may be described herein in terms of functional and/or logical block components, and with reference to symbolic representations of certain operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in a processor-readable medium or transmitted by a computer data signal embodied in a carrier wave over a transmission medium or communication path. The "computer-readable medium," "processor-readable medium," or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

For the sake of brevity, conventional techniques related to signal processing, data transmission, signaling, network control, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented in software for execution by various types of processors. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module.

A module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method for detecting and correcting drift associated with operation of a hybrid tracking system, the method comprising:
   obtaining a data signal from a first tracker subsystem having a first tracker latency time;
   for a defined window of time,
      capturing snapshot input data for a second tracker subsystem having a second tracker latency time which is longer than the first tracker latency time; and
      capturing synchronized data from the data signal which corresponds to the defined window of time;
      wherein the defined window of time comprises a time duration shorter than the second tracker latency time, to capture the snapshot input data;
   calculating second tracker snapshot results from the captured snapshot input data for the second tracker subsystem;
   calculating first tracker snapshot results from the captured synchronized data from the first tracker subsystem;
   calculating an error between the first tracker snapshot results and the second tracker snapshot results, to determine a level of drift associated with operation of the first tracker subsystem; and
   adjusting operation of the first tracker subsystem according to the determined level of drift.

2. The method of claim 1, wherein the first tracker snapshot results comprise an inertial estimate of position, relative to a reference frame, from the first tracker subsystem; and
   wherein the second tracker snapshot results comprise a non-inertial estimate of position from the second tracker subsystem.

3. The method of claim 1, wherein the adjusting step further comprises adding a translational offset to an output signal, and wherein the translational offset comprises the calculated error,
   wherein the data signal comprising the output signal.

4. The method of claim 1, wherein the adjusting step further comprises performing a rotational computation using an output signal, and wherein the rotational computation comprises the calculated error,
   wherein the data signal comprising the output signal.

5. The method of claim 1, further comprising:
   determining whether the calculated error comprises a result consistent with a previously calculated error; and
   performing the adjusting step when the calculated error and the previously calculated error comprise consistent values.

6. The method of claim 1, further comprising:
   determining whether the calculated error comprises a result consistent with a plurality of previously calculated errors; and
   performing the adjusting step when the calculated error and the previously calculated errors comprise consistent values.

7. The method of claim 1, wherein the second tracker latency time comprises a duration of time greater than ten times longer than the first tracker latency time.

8. The method of claim 1, further comprising:
   calculating a weighted average of the calculated error and a plurality of previously calculated errors; and
   determining the level of drift based on the calculated weighted average.

9. A head-worn display apparatus, configured to provide a conformal near-to-eye (NTE) display, the apparatus comprising:
   a hybrid tracking system, comprising:
      an inertial tracker, configured to provide first positional data of the head-worn display apparatus, with regard to an inertial reference frame;
      a non-inertial tracker, configured to provide second positional data of the head-worn display apparatus, with regard to the inertial reference frame;
   a snapshot module, configured to:
      determine a snapshot time frame by coordinating a window of time for gathering input data for the non-inertial tracker;
      synchronize operation of the inertial tracker and the non-inertial tracker; and
      capture a relevant subset of the first positional data associated with the determined snapshot time frame and a relevant subset of the second positional data associated with the determined snapshot time frame;
   a drift detection module, configured to compare the relevant subset of first positional data with the relevant subset of second positional data, to determine an offset; and
   a drift correction module, configured to adjust operation of the inertial tracker, based on the determined offset.

10. The system of claim 9, wherein synchronizing operation of the inertial tracker and the non-inertial tracker further comprises synchronizing a data signal of the inertial tracker with an input signal of the non-inertial tracker.

11. The system of claim 9, wherein the non-inertial tracker comprises an optical tracker.

12. The system of claim 9, wherein the non-inertial tracker comprises a magnetic tracker.

13. The system of claim 9, wherein the determined offset comprises error associated with one or more orientational degrees of freedom (DOF); and
   wherein the adjustment of the operation of the inertial tracker comprises performing a rotational computation to accommodate the error associated with one or more DOF.

14. The system of claim 9, wherein the determined offset comprises a translational error; and
   wherein the adjustment of the operation of the inertial tracker comprises adding the offset to the first positional data to accommodate the translational error.

15. A non-transitory, computer-readable medium containing instructions thereon, which, when executed by a processor, perform a method comprising:
   synchronizing an inertial tracker and a non-inertial tracker;
   identifying a snapshot time-frame, based on the synchronization step;
   during the snapshot time-frame, obtaining input data for the non-inertial tracker;
   obtaining data from the inertial tracker corresponding to the snapshot time-frame;
   obtaining a first result from the inertial tracker and a second result from the non-inertial tracker, each representative of the snapshot time-frame;
   comparing the first result to the second result to obtain a discrepancy result; and
   modifying operation of the inertial tracker, based on the discrepancy result.

16. The non-transitory, computer-readable medium of claim 15, wherein the synchronizing step further comprises synchronizing an output signal of the inertial tracker to an input signal of the non-inertial tracker; and
   wherein the first result comprises the output signal.

17. The non-transitory, computer-readable medium of claim 15, wherein the identifying step further comprises coordinating the snapshot time-frame based upon the latency time associated with the non-inertial tracker, detected drift rates, and desired measurement accuracies.

18. The non-transitory, computer-readable medium of claim 15, wherein the comparing step further comprises calculating a difference between the first result and the second result for each of a plurality of degrees of freedom (DOF), and wherein the discrepancy result comprises the calculated difference for each of the DOF.

19. The non-transitory, computer-readable medium of claim 15, wherein the discrepancy result comprises a drift offset value; and
   wherein the modifying step further comprises adding the drift offset value to the first result to generate a corrected output signal from the inertial tracker.

20. The non-transitory, computer-readable medium of claim 15, wherein the discrepancy result comprises a drift offset value; and
   wherein the modifying step further comprises performing a rotational computation using the drift offset value, to generate a corrected output signal from the inertial tracker.

* * * * *